United States Patent [19]

Grasselli et al.

[11] 3,993,680

[45] Nov. 23, 1976

[54] AMMOXIDATION USING CHROMIUM-CONTAINING CATALYSTS

[75] Inventors: Robert K. Grasselli, Chagrin Falls; Arthur F. Miller; Wilfrid G. Shaw, both of Lyndhurst, all of Ohio

[73] Assignee: The Standard Oil Company (Ohio), Cleveland, Ohio

[22] Filed: Dec. 18, 1974

[21] Appl. No.: 532,096

Related U.S. Application Data

[62] Division of Ser. No. 393,732, Sept. 4, 1973, Pat. No. 3,956,181.

[52] U.S. Cl. ............................ 260/465.3; 260/533 N; 260/604 R; 260/680 E
[51] Int. Cl.² .................................... C07C 120/14
[58] Field of Search ........................... 260/465.3

[56] References Cited

UNITED STATES PATENTS

| | | |
|---|---|---|
| 3,135,783 | 6/1964 | Sennewald et al. ............... 260/465.3 |
| 3,342,849 | 9/1967 | Brill et al. ........................ 260/465.3 |
| 3,347,899 | 10/1967 | Caporali et al. .................. 260/465.3 |
| 3,625,867 | 12/1971 | Yoshino et al. ................ 260/465.3 X |
| 3,642,930 | 2/1972 | Grasselli et al. ............. 260/465.3 X |
| 3,872,148 | 3/1975 | Umemura et al. ................ 260/465.3 |

OTHER PUBLICATIONS

Dalin et al., "Acrylonitrile", 1971, pp. 70–91, Progress in Materials Science Series, vol. VI.

Primary Examiner—Joseph Paul Brust
Attorney, Agent, or Firm—Herbert D. Knudsen; Larry W. Evans; Gwenetta D. Hill

[57] ABSTRACT

Catalysts containing at least nickel or cobalt, chromium, bismuth and molybdenum have been found to be especially useful for the ammoxidation of olefins, the oxidation of olefins and the oxidative dehydrogenation of olefins.

6 Claims, No Drawings

AMMOXIDATION USING CHROMIUM-CONTAINING CATALYSTS

This is a divisional of application Ser. No. 393,732 filed Sept. 4, 1973 now U.S. Pat. No. 3,956,181.

BACKGROUND OF THE INVENTION

The ammoxidation of olefins, oxidative dehydrogenation of olefins and oxidation of olefins with catalysts similar to those of the present invention are known. See for example, U.S. Pat. No. 3,642,930, U.S. Pat. No. 3,414,631, Ser. No. 85,722 filed Oct. 30, 1970, and U.S. Pat. No. 3,576,764.

The catalysts of the present invention have a composition different from those of the art and are very selective catalysts even at high temperatures.

SUMMARY OF THE INVENTION

The present invention is a catalyst composition having the empirical formula $$A_a D_b Ni_c Co_d Cr_e Bi_f Mo_{12} O_x$$

wherein

A is an alkali metal, Tl, In, Ag, Cu, rare earth or mixture thereof; and

D is P, As, Sb, Sn, Ge, B, W, Th, V, Ti, Si or mixture thereof;

and wherein a and b are 0-4;

c and d are 0 to 20 with c + d greater than or equal to 0.1;

e is 0.1 to about 10;

f is about 0.01 to 6; and x is the number of oxygens required to satisfy the valence requirements of the other elements present.

These catalysts have been found to be especially useful for the ammoxidation, oxidation and oxidative dehydrogenation of olefins.

The central aspect of the present invention is the catalyst. The catalyst can be any of the catalysts delimited by the general formula above. Preferred are those catalysts that contain an alkali metal and those catalysts that contain both nickel and cobalt.

The catalysts of the invention are conveniently prepared by any of the methods associated with the similar oxidation catalysts in the art. Among the methods of combining the elements of the catalyst are the coprecipitation of soluble salts from a solution and the mixing of salts or oxides of the various compounds. After the elements of the catalyst are combined, the preparation of the catalyst is completed by calcination of the catalyst at an elevated temperature. Temperatures between about 200° and about 700° C. are most suitable.

Specific preparations of catalysts of the invention are shown in the Specific Embodiments. These preparations are given preferred catalysts of the invention.

The catalysts of the invention may be used as pure catalytic material or they may be used in the supported form. Suitable support materials include silica, alumina, titania, zirconia, boron phosphate and the like. The use of catalysts supported on silica is preferred.

The catalysts of the invention have utility for a broad range of oxidation, ammoxidation and oxidative dehydrogenation reactions. Preferred are the ammoxidation of propylene or isobutylene, the oxidation of propylene or isobutylene and the oxidative dehydrogenation of olefins containing about 4 to about 10 carbon atoms.

The reactions in which the catalysts of the invention are utilized are well known. Essentially, the invention with respect to these processes is the use of the new catalyst of the invention within the parameters of the known process. Broadly, the processes all utilize molecular oxygen, preferably air, in the reactant feed, and the reactions are normally conducted within the range of about 200° to about 600° C. with temperatures of about 300° C. to about 500° C. being preferred. The reactant ratios may vary as the different reactions are conducted but generally range within about 5 to about 15 moles of air per mole of olefin.

The reactions can be run at atmospheric, superatmospheric or subatmospheric pressures using contact times of a fraction of a second to 20 seconds or more. The reactions can be run in a fixed-bed or fluid-bed reactor. In a fluid-bed reactor, the catalyst is normally used in the form of pellets, tablets or spheres and the like. In a fluid-bed reactor, the catalyst is small particles, such as microspheroids, that are fluidized in the reaction.

As noted above, the catalysts of the invention are very selective even at high temperatures. Thus, high temperatures can be used in the reaction without a substantial adverse effect on the desired yield of the reaction. The catalysts exhibit high per pass conversions to useful products at high reactant through-put.

SPECIFIC EMBODIMENTS

EXAMPLES 1 – 15

Ammoxidation of propylene.

A reactor was constructed of a stainless tube having an inside diameter of 0.8 cm., an inlet for reactants and an outlet for products. The reactor had a catalytic reaction zone having a volume of 5 cc. and was externally heated.

Various catalyst compositions containing 80% active catalytic ingredients and 20% SiO$_2$ were prepared as follows:

EXAMPLES 1–3

$K_{0.1}Ni_{2.5}Co_{4.5}Cr_3BiP_{0.5}Mo_{12}O_x$ In 30 cc. of warm water 31.8 g. of ammonia heptamolybdate, $(NH_4)_6Mo_7O_{24}\cdot 4H_2O$, were dissolved and 26.8 g. of 40% silica sol were added. With constant stirring, the mixture was slowly heated for about 5 minutes, and 0.9 g. of 85% phosphoric acid, 10.9 g. of nickel nitrate, Ni(No$_3$)$_2$·6H$_2$O and 19.7 g. of cobalt nitrate, Co(No$_3$)$_2$·6H$_2$O, were sequentially added. Heating and stirring were continued for a few minutes.

Separately, an aqueous mixture containing 18.0 g. of chromium nitrate, Cr(NO$_3$)$_3$·9H$_2$O, 7.2 g. of bismuth nitrate, Bi(NO$_3$)$_3$·5H$_2$O and 0.19 g. of a 45% solution of potassium hydroxide was prepared. This second mixture was slowly added to the first slurry on a hot plate. After the addition was complete, the heat was increased until the mixture started to thicken. The resultant thick paste was dried in a drying oven at 120° C. with occasional stirring. The dried catalyst was then heat treated at 550° C. for 20 hours.

EXAMPLES 4 and 5

$K_{0.1}Ni_2Co_4Cr_3BiMo_{12}O_x$ In 60 cc. of warm water 63.56 g. of ammonium heptamolybdate was dissolved and 50.90 g. of 40% silica sol was added to form a slurry.

Separately, 9.00 g. chromium oxide, CrO$_3$, 14.55 g. bismuth nitrate, 34.93 g. of cobalt nitrate, 17.45 g. nickel nitrate and 3.03 g. of a 10% solution of potassium nitrate were combined in an aqueous mixture. The aqueous mixture was slowly added to the slurry, and the resultant mixture was heated on a hot plate until it began to thicken. The paste was dried at 120° C. and then calcined at 550° C. for 16 hours.

EXAMPLES 6 and 7

$K_{0.1}Ni_7Cr_3BiP_{0.5}Mo_{12}O_x$ A slurry was made by dissolving 63.56 g. of ammonium heptamolybdate in 60 cc. of warm water and adding 52.95 g. of 40% silica sol and 3.46 g. of a 42.5% solution of phosphoric acid.

Separately, in a small amount of water on a hot plate 9.00 g. of chromium oxide, 61.07 g. of nickel nitrate, 3.03 g. of a 10% solution of potassium nitrate and 14.55 g. of bismuth nitrate were dissolved. The resultant solution was slowly added to the slurry with heating. When the mixture started to thicken, it was removed from the hot plate and placed in an oven at 120° C. The dried material was heated at 290° C. for 3 hours, at 425° C. for 3 hours and at 550° C. for 16 hours.

EXAMPLES 8 and 9

$K_{0.1}Co_7Cr_3BiP_{0.5}Mo_{12}O_x$ The catalyst was prepared in exactly the same way as Examples 6 and 7 except that 61.12 g. of cobalt nitrate was substituted for the nickel nitrate.

EXAMPLE 10

$Ge_{0.5}K_{0.1}Ni_{2.5}Co_{4.5}Cr_3BiMo_{12}O_x$ An aqueous slurry was prepared using 63.56 g. of ammonium heptamolybdate, 53.28 g. of 40% silica sol and 1.57 g. of germanium oxide, $GeO_2$.

An aqueous solution was formed using 9.00 g. chromium oxide, 14.55 g. bismuth nitrate, 39.29 g. cobalt nitrate, 21.80 g. of nickel nitrate and 3.03 g. of a 10% solution of potassium nitrate. The combining of the mixtures, drying and calcination were conducted as shown in Examples 6 and 7.

EXAMPLE 11

$Sn_{0.5}K_{0.1}Ni_{2.5}Co_{4.5}Cr_3BiMo_{12}O_x$ The catalyst was prepared as shown in Example 10 substituting 1.75 cc. of stannic chloride, $SnCl_4$, for the germanium oxide.

EXAMPLE 12

$B_{0.5}K_{0.1}Ni_{2.5}Co_{4.5}Cr_3BiMo_{12}O_x$ The catalyst was prepared as shown in Example 10 substituting 0.93 g. of boric acid for the germanium oxide.

EXAMPLE 13

$W_{0.5}K_{0.1}Ni_{2.5}Co_{4.5}Cr_3BiMo_{12}O_x$ The catalyst was prepared as shown in Example 10 substituting 4.05 g. $(NH_4)_6W_7O_{24}.6H_2O$ for the germanium oxide.

EXAMPLE 14

$V_{0.5}K_{0.1}Ni_{2.5}Co_{4.5}Cr_3BiMo_{12}O_x$ The catalyst was prepared as described in Example 10 substituting 1.75 g. of $NH_4VO_3$ for the germanium oxide and 22.24 g. chromium acetate, $Cr(C_2H_3O_2)_3.H_2O$ for the chromium oxide.

EXAMPLE 15

$Cu_{0.1}K_{0.1}Ni_{2.5}Co_{4.5}Cr_3BiP_{0.5}Mo_{12}O_x$ The catalyst was prepared as shown in Example 10 except that chromium acetate was added as in Example 14, and 3.46 g. of a 42.5% solution of phoshoric acid was added in place of the germanium oxide and 0.72 g. of $Cu(NO_3)_2.3H_2O$ was added to the second solution.

In preparation for use, the catalysts were ground and screened to give a 20 to 35 mesh fraction. Five cc. of this catalyst was placed in the catalytic reactor, and the ammoxidation of propylene was conducted using a feed of propylene/ammonia/air/steam of 1/1.1/10/4 and an apparent contact time of six seconds. The results of these experiments are shown in Table I. It will be noted that even though the temperature is increased, the selectivity remains remarkably stable. It would be expected that at these high temperatures, the selectivity would rapidly decline.

The results are stated in the following terms:

$$\% \text{ conversion} = \frac{\text{amount of olefin reacted} \times 100}{\text{amount of olefin fed}}$$

$$\% \text{ selectivity} = \frac{\text{amount of product obtained} \times 100}{\text{amount of olefin reacted}}$$

$$\% \text{ single pass yield} = \frac{\text{amount of product obtained} \times 100}{\text{amount of olefin fed}}$$

Table I

| | AMMOXIDATION OF PROPYLENE | | | | |
|---|---|---|---|---|---|
| | | | Results, % | | |
| Example | Catalyst | Temp. ° C. | Conversion | Selectivity | Single Pass Yield |
| 1 | $K_{0.1}Ni_{2.5}Co_{4.5}Cr_3BiP_{0.5}Mo_{12}O_x$ | 420 | 62.4 | 89 | 55.7 |
| 2 | '' | 440 | 88.7 | 83 | 73.9 |
| 3 | '' | 460 | 95.9 | 81 | 77.8 |
| 4 | $K_{0.1}Ni_2Co_4Cr_3BiMo_{12}O_x$ | 440 | 85.5 | 75 | 63.9 |
| 5 | '' | 460 | 95.7 | 71 | 68.3 |
| 6 | $K_{0.1}Ni_7Cr_3BiP_{0.5}Mo_{12}O_x$ | 440 | 93.9 | 79 | 74.2 |
| 7 | '' | 460 | 98.2 | 78 | 76.7 |
| 8 | $K_{0.1}Co_7Cr_3BiP_{0.5}Mo_{12}O_x$ | 440 | 61.3 | 82 | 50.4 |
| 9 | '' | 460 | 74.7 | 80 | 5919 |
| 10 | $Ge_{0.5}(K_{0.1}Ni_{2.5}Co_{4.5}Cr_3BiMo_{12}O_x)$ | 460 | 88.3 | 77 | 68.2 |
| 11 | $Sn_{0.5}(K_{0.1}Ni_{2.5}Co_{4.5}Cr_3BiMo_{12}O_x)$ | '' | 90.3 | 71 | 64.4 |
| 12 | $B_{0.5}(K_{0.1}Ni_{2.5}Co_{4.5}Cr_3BiMo_{12}O_x)$ | '' | 89.9 | 76 | 68.4 |
| 13 | $W_{0.5}(K_{0.1}Ni_{2.5}Co_{4.5}Cr_3BiMo_{12}O_x)$ | '' | 96.4 | 76 | 73.4 |
| 14 | $V_{0.5}(K_{0.1}Ni_{2.5}Co_{4.5}Cr_3BiMo_{12}O_x)$ | '' | 100 | 76 | 75.8 |
| 15 | $Cu_{0.1}P_{0.5}(K_{0.1}Ni_{2.5}Co_{4.5}Cr_3BiMo_{12}O_x)$ | '' | 99.1 | 80 | 78.8 |

EXAMPLES 16-24

Oxidative dehydrogenation of butene.

The catalyst prepared for Examples 1–3 was heat treated for an additional three hours at 650° C. To the reactor, as described above, was charged 2.5 cc. of the catalyst. A feed of butene-1/air/steam of 1/11/4 was passed over the catalyst for an apparent contact time of one second.

The results are given in Table II. The conversion and selectivity figures given ignores the isomerization of butene-1 to butene-2 by calculating butene-2 as unreacted reactant.

Table II

| OXIDATIVE DEHYDROGENATION OF BUTENE-1 | | | | |
|---|---|---|---|---|
| | | Results, % | | |
| Example | Temp., °C. | Conversion | Selectivity | Single Pass Yield |
| 16 | 350 | 48.4 | 99 | 48.1 |
| 17 | 400 | 70.1 | 99 | 69.3 |
| 18 | 420 | 77.3 | 98 | 76.4 |
| 19 | 440 | 83.8 | 94 | 79.0 |
| 20 | 460 | 89.0 | 93 | 82.7 |
| 21 | 480 | 92.6 | 91 | 84.6 |
| 22 | 500 | 95.5 | 87 | 83.1 |
| 23[1] | 400 | 78.6 | 98 | 76.8 |
| 24[2] | 440 | 92.4 | 93 | 85.5 |

[1] feed: 1 butene-1/27 air/4 steam contact time 1.5 sec.
[2] no steam added

EXAMPLES 25-39

Oxidative dehydrogenation of butene-1 with various catalysts.

The catalysts prepared as described in Examples 1-15 were used to oxidative dehydrogenate butene-1 using a feed of butene-1/air/stream of 1/11/4 and an apparent contact time of one second. The results are shown in Table III.

A catalyst of the formula 80% $Sn_{0.5}K_{0.1}Ni_{2.5}Co_{4.5}Cr_{2.5}BiP_{0.5}Mo_{12}O_x$ and 20% $SiO_2$ was prepared in a manner substantially the same as the catalyst for Example 11 except that the amount of chromium was reduced and phosphoric acid was added to the solution.

In an oxidative dehydrogenation of butene-1 using 11 moles of air per mole of butene-1 and no steam at 440° C. and a contact time of one second, the conversion was 90.8%, the selectivity was 91% and the per pass conversion was 82.7%.

EXAMPLE 42

Preparation of acrolein and acrylic acid.

A catalyst prepared according to Example 15 was used for the oxidation of propylene using a feed of propylene/air/steam of 1/11/4. At a temperature of 400° C. and a contact time of 6 seconds, the conversion was 82.8%, the selectivity to acrolein and acrylic acid was 85%, the single pass yield to acrolein was 66.7% and the single pass yield to acrylic acid was 3.5%.

EXAMPLE 43

Preparation of methacrylonitrile.

In the same manner as described for the ammoxidation of propylene, isobutylene was reacted to form methacrylonitrile. Using a reactant feed of isobutylene/ammonia/air/steam of 1/1.5/10/4 at a temperature of 400° C. and an apparent contact time of 6 seconds, the single pass yield of methacrylonitrile was 56.9%.

In the same manner as described by the examples above butene-2 or isoamylene is oxidatively dehydro- Table III

| OXIDATIVE DEHYDROGENATION OF BUTENE-1 | | | | | |
|---|---|---|---|---|---|
| | | | Results, % | | |
| Example | Catalyst | Temp., °C. | Conversion | Selectivity | Single Pass Yield |
| 25 | $K_{0.1}Ni_2Co_4Cr_3BiMo_{12}O_x$ | 420 | 77.7 | 93 | 72.4 |
| 26 | " | 440 | 85.8 | 92 | 79.0 |
| 27 | $K_{0.1}Ni_7Cr_3BiP_{0.5}Mo_{12}O_x$ | 420 | 82.7 | 94 | 78.1 |
| 28 | " | 440 | 87.6 | 91 | 80.0 |
| 29 | $K_{0.1}Co_7Cr_3BiP_{0.5}Mo_{12}O_x$ | 420 | 77.3 | 83 | 63.9 |
| 30 | " | 440 | 79.8 | 81 | 64.5 |
| 31 | $K_{0.1}Ni_{2.5}Co_{4.5}Cr_3BiP_{0.5}Mo_{12}O_x$ | 420 | 78.6 | 96 | 75.7 |
| 32 | " | 440 | 86.0 | 95 | 81.5 |
| 33 | $Ge_{0.5}(K_{0.1}Ni_{2.5}Co_{4.5}Cr_3BiMo_{12}O_x)$ | " | 79.2 | 94 | 74.3 |
| 34 | $Sn_{0.5}(K_{0.1}Ni_{2.5}Co_{4.5}Cr_3BiMo_{12}O_x)$ | " | 81.5 | 91 | 73.8 |
| 35 | $B_{0.5}(K_{0.1}Ni_{2.5}Co_{4.5}Cr_3BiMo_{12}O_x)$ | " | 80.3 | 95 | 76.3 |
| 36 | $W_{0.5}(K_{0.1}Ni_{2.5}Co_{4.5}Cr_3BiMo_{12}O_x)$ | " | 83.8 | 95 | 79.8 |
| 37 | $V_{0.5}(K_{0.1}Ni_{2.5}Co_{4.5}Cr_3BiMo_{12}O_x)$ | " | 87.3 | 77 | 67.6 |
| 38 | $Cu_{0.1}P_{0.5}(K_{0.1}Ni_{2.5}Co_{4.5}CrBiMo_{12}O_x)$ | " | 90.0 | 96 | 86.3 |
| 39* | " | " | 92.4 | 93 | 85.5 |

*no steam added to feed

EXAMPLE 40

Catalyst without alkali metal.

A catalyst was prepared according to the method for the catalyst of Examples 1-3 except that potassium was omitted from the preparation. The catalyst had the formula 80% $Ni_{2.5}Co_{4.5}Cr_3BiP_{0.5}Mo_{12}O_x$ + 20% $SiO_2$.

In the same manner as described above, butene-1 was oxidatively dehydrogenated using a feed of 1 butene-1/11 air/ 4 steam at 420° C. and an apparent contact time of one second. The conversion of the butene-1 was 84.1%, the selectivity to butadiene was 87% and the single pass yield was 73.2%.

EXAMPLE 41

Tin containing catalyst.

genated with similar results. Also, in the same manner, isobutylene is oxidized to methacrolein using the catalysts of the invention.

We claim:

1. In the process for the ammoxidation of propylene or isobutylene to produce acrylonitrile or methacrylonitrile comprising contacting the propylene or isobutylene with ammonia and molecular oxygen in the presence of a catalyst at a temperature of about 200° to about 600° C., the improvement comprising using as the catalyst the catalyst of the formula
$$A_a D_b Ni_c Co_d Cr_e Bi_f Mo_{12} O_x$$
wherein
A is an alkali metal, Tl, In, Ag, Cu, rare earth metal or mixture thereof; and
D is P, As, Sb, Sn, Ge, B, W, Th, V, Ti, Si or mixture thereof;
and wherein $a$ and $b$ are 0–4;
$c$ and $d$ are 0 to 20 with $c + d$ greater than or equal to 0.1;
$e$ is 0.1 to about 10;
$f$ is about 0.01 to 6; and
$x$ is the number of oxygens required to satisfy the valence requirements of the other elements present.

2. The process of claim 1 wherein the catalyst contains an alkali metal.

3. The process of claim 1 wherein the catalyst contains potassium.

4. The process of claim 1 wherein the catalyst contains nickel and cobalt.

5. The process of claim 1 wherein the catalyst is $K_{0.1}Ni_{2.5}Co_{4.5}Cr_3BiP_{0.5}Mo_{12}O_x$.

6. The process of claim 4 wherein the catalyst is promoted with copper.

* * * * *

UNITED STATES PATENT OFFICE
CERTIFICATE OF CORRECTION

Patent No. 3,993,680    Dated November 23, 1976

Inventor(s) Robert K. Grasselli et al

It is certified that error appears in the above-identified patent and that said Letters Patent are hereby corrected as shown below:

Column 5: Example 39 in Table III

"$Cu_{0.1}P_{0.5}(K_{0.1}Ni_{2.5}Co_{4.5}CrBiMo_{12}O_x)$" should be --

--$Cu_{0.1}P_{0.5}(K_{0.1}Ni_{2.5}Co_{4.5}Cr_3BiMo_{12}O_x)$ --

Signed and Sealed this

*Twenty-fifth* Day of *October 1977*

[SEAL]

*Attest:*

RUTH C. MASON  
*Attesting Officer*

LUTRELLE F. PARKER  
*Acting Commissioner of Patents and Trademarks*